(12) United States Patent
Zuber et al.

(10) Patent No.: US 11,260,184 B2
(45) Date of Patent: Mar. 1, 2022

(54) INHALER WITH SIZED CAVITY

(71) Applicant: PHILIP MORRIS PRODUCTS S.A., Neuchâtel (CH)

(72) Inventors: Gerard Zuber, Neuchâtel (CH); Waller Judith, Ostersund (SE); Gennaro Campitelli, Bologna (IT)

(73) Assignee: Philip Morris Products S.A., Neuchatel (CH)

( * ) Notice: Subject to any disclaimer, the term of this patent is extended or adjusted under 35 U.S.C. 154(b) by 336 days.

(21) Appl. No.: 16/464,790

(22) PCT Filed: Nov. 17, 2017

(86) PCT No.: PCT/IB2017/057220
§ 371 (c)(1),
(2) Date: May 29, 2019

(87) PCT Pub. No.: WO2018/100462
PCT Pub. Date: Jun. 7, 2018

(65) Prior Publication Data
US 2019/0282769 A1 Sep. 19, 2019

(30) Foreign Application Priority Data
Nov. 30, 2016 (EP) ..................................... 16201578

(51) Int. Cl.
*A61M 15/00* (2006.01)
*A61M 15/06* (2006.01)
*A61K 31/465* (2006.01)

(52) U.S. Cl.
CPC ......... *A61M 15/003* (2014.02); *A61K 31/465* (2013.01); *A61M 15/0005* (2014.02);
(Continued)

(58) Field of Classification Search
CPC .......... A61M 15/0005; A61M 15/0006; A61M 15/0008; A61M 15/003; A61M 15/0035;
(Continued)

(56) References Cited

U.S. PATENT DOCUMENTS 2,569,720 A * 10/1951 Jesnig ............... A61M 15/0028
128/203.15
2,722,935 A * 11/1955 Thompson ............ B05B 11/062
128/203.15
(Continued)

FOREIGN PATENT DOCUMENTS

CA 2509521 A1 * 6/2004 ........ A61M 15/0005
CN 2014910375 U 12/2015
(Continued)

OTHER PUBLICATIONS

Chinese Office Action issued in CN Application No. 201780068583.3 by the China National Intellectual Property Administration, dated Mar. 17, 2021; 16 pgs. including English Translation.
(Continued)

*Primary Examiner* — Kathryn E Ditmer
(74) *Attorney, Agent, or Firm* — Mueting Raasch Group

(57) ABSTRACT

An inhaler article includes a body extending along a longitudinal axis from a mouthpiece end to a distal end and a capsule cavity defined within the body. The capsule cavity has a length extending along the longitudinal axis. A mouthpiece air channel extends from the capsule cavity to the mouthpiece end. An end cap is disposed within the distal end and extends to the capsule cavity. The end cap includes an air channel extending from the end cap distal end to the end cap inner end. A capsule is disposed within the capsule cavity and has a capsule length. The capsule length is in a range from about 25% to about 99% of the cavity length, or about 50% to about 95% of the cavity length, or about 70% to about 90% of the cavity length, or from about 75% to
(Continued)

Figure 1:
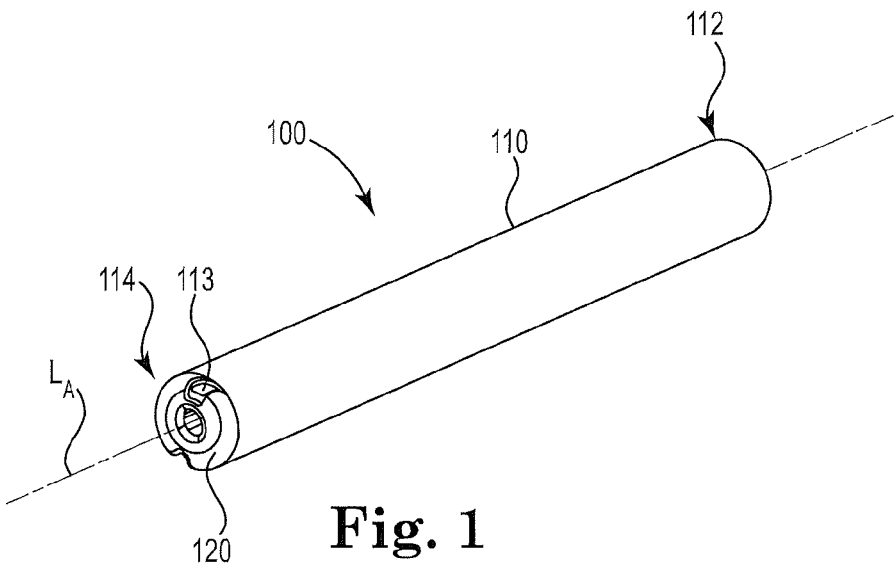
Figure 2:
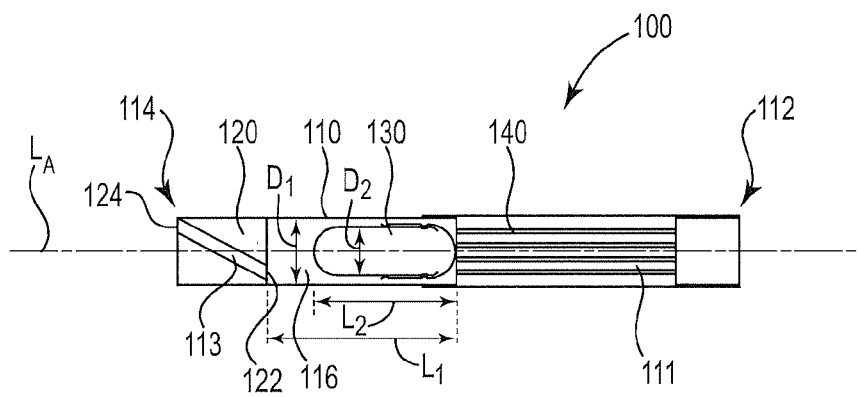
Figures 3A, 3B, 4A, 4B:
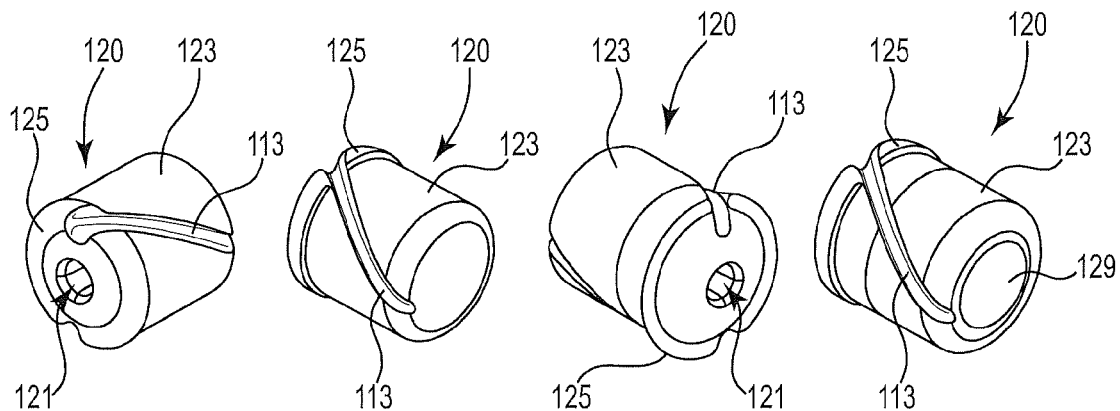
Figure 5:
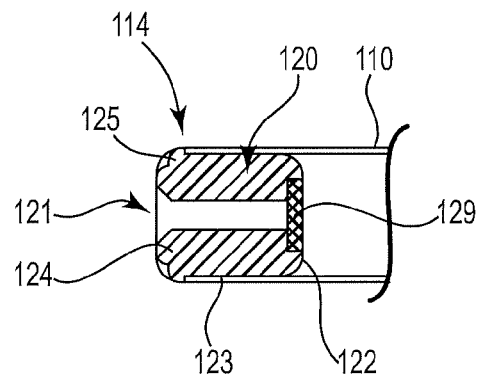
Figure 6:
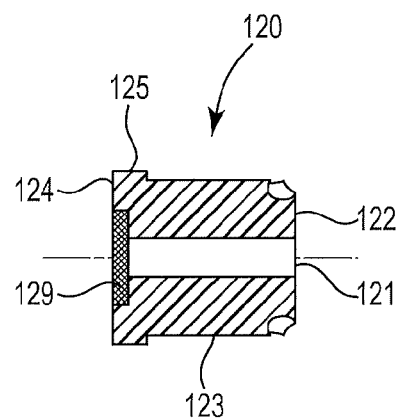

about 85% of the cavity length, or about 80% of the cavity length.

20 Claims, 2 Drawing Sheets

(52) U.S. Cl.
CPC ........ *A61M 15/0028* (2013.01); *A61M 15/06* (2013.01); *A61M 2202/064* (2013.01); *A61M 2206/16* (2013.01)

(58) Field of Classification Search
CPC ............ A61M 15/0036; A61M 15/004; A61M 15/0041; A61M 2202/064; A61M 2206/16; A24F 42/20
See application file for complete search history.

(56) References Cited

U.S. PATENT DOCUMENTS

| | | | | |
|---|---|---|---|---|
| 2,946,332 | A * | 7/1960 | Sacks | A61M 15/0041 128/203.15 |
| 3,888,252 | A * | 6/1975 | Side | A61M 15/0033 128/203.15 |
| 3,991,761 | A | 11/1976 | Cocozza | |
| 4,064,878 | A * | 12/1977 | Lundquist | A61M 15/0036 128/203.15 |
| 4,069,819 | A * | 1/1978 | Valentini | A61M 15/0028 128/203.15 |
| 4,889,114 | A * | 12/1989 | Kladders | A61M 15/0028 128/203.15 |
| 4,995,385 | A * | 2/1991 | Valentini | A61M 15/0028 128/203.15 |
| 5,727,546 | A | 3/1998 | Clarke et al. | |
| 5,797,391 | A | 8/1998 | Cook et al. | |
| 6,123,070 | A * | 9/2000 | Bruna | A61M 15/0065 128/203.12 |
| 6,705,313 | B2 * | 3/2004 | Niccolai | A61M 15/0008 128/203.21 |
| 7,810,494 | B2 * | 10/2010 | Harmer | A61M 15/0048 128/203.21 |
| 8,869,794 | B1 * | 10/2014 | Tuckwell | A61M 15/0035 128/203.21 |
| 2002/0062829 | A1 * | 5/2002 | Ohki | A61M 15/003 128/203.15 |
| 2003/0094173 | A1 | 5/2003 | Burr et al. | |
| 2004/0173211 | A1 | 9/2004 | Kladders et al. | |
| 2004/0206350 | A1 * | 10/2004 | Alston | A61M 15/0033 128/203.12 |
| 2007/0240713 | A1 * | 10/2007 | Boeck | A61P 43/00 128/203.15 |
| 2013/0327327 | A1 | 12/2013 | Edwards et al. | |
| 2014/0060535 | A1 * | 3/2014 | Tsutsui | A61M 15/0043 128/203.15 |
| 2014/0076315 | A1 * | 3/2014 | Von Schuckmann | A61M 15/0035 128/203.15 |
| 2014/0150787 | A1 * | 6/2014 | Ellwanger | A61P 25/16 128/203.15 |
| 2014/0182587 | A1 * | 7/2014 | Dunne | A61M 15/0086 128/203.15 |
| 2015/0027468 | A1 * | 1/2015 | Li | A24D 3/048 131/329 |
| 2015/0059747 | A1 * | 3/2015 | Von Schuckmann | A61M 15/0026 128/203.15 |
| 2015/0196060 | A1 * | 7/2015 | Wensley | A24F 40/48 392/390 |
| 2016/0129205 | A1 * | 5/2016 | Shahaf | B05B 11/062 128/200.23 |
| 2017/0042251 | A1 * | 2/2017 | Yamada | A24F 40/50 |

FOREIGN PATENT DOCUMENTS

| | | | |
|---|---|---|---|
| DE | 102006006647 B3 * | 1/2007 | .......... A61M 15/004 |
| EP | 2399637 A1 | 12/2011 | |
| JP | 2006522663 A | 10/2006 | |
| RU | 121737 U1 | 11/2012 | |
| WO | 2004091705 A1 | 10/2004 | |
| WO | WO 2015/166350 A2 | 11/2015 | |
| WO | 2015193498 | 12/2015 | |
| WO | 2016168266 | 10/2016 | |

OTHER PUBLICATIONS

Russian Office Action and Search Report issued in RU Application No. 2019116591 by the Russian Federal Service on Intellectual Property, dated Apr. 7, 2021; 10 pgs. including English Translation.
Extended European Search Report for EP 16201578.8, issued by the European Patent Office dated Jan. 23, 2017; 8 pgs.
International Search Report and Written Opinion for PCT/IB2017/057220; issued by the European Patent Office dated Mar. 5, 2018; 19 pgs.
International Preliminary Report on Patentability for PCT/IB2017/057220; issued by the European Patent Office dated Feb. 1, 2019; 18 pgs.
Hall, R.L. & Oser, B.L., "Recent Progress in the Consideration of Flavoring Ingredients under the Food Additive Amendments 3. GRAS substances," *Food Technology*, Feb. 1965: p. 151-197.
Cohen et al., "GRAS Flavoring Substances," 27. *GRAS Flavoring Substances. Food Technology for Flavoring Extract Manufacturers Association*, Aug. 2015:69(8):40-59.
Japanese Office Action for JP 2019-52880 issued by the Japanese Patent Office dated Sep. 8, 2021; 4 pgs. including English Translation.

* cited by examiner

INHALER WITH SIZED CAVITY

This application is the § 371 U.S. National Stage of International Application No. PCT/IB2017/057220, filed 17 Nov. 2017, which claims the benefit of European Application No. 16201578.8, filed 30 Nov. 2016, the disclosures of which are incorporated by reference herein in their entireties.

This disclosure relates to an inhaler article that includes an air inlet channel that extends through an end cap to a capsule cavity that is sized to a capsule therein.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose in a single breath.

It would be desirable to provide a nicotine powder inhaler that provides nicotine particles to the lungs at inhalation or air flow rates that are within conventional smoking regime inhalation or air flow rates. It would also be desirable to provide deliver the nicotine powder inhaler with an inhaler article that has a form similar to a conventional cigarette. It would also be desirable to provide an inhaler article that is simple to manufacture and convenient to use by a consumer.

This disclosure is directed to an inhaler article comprising a body extending along a longitudinal axis from a mouthpiece end to a distal end and a capsule cavity is defined within the body. A mouthpiece air channel extends from the capsule cavity to the mouthpiece end. An end cap is disposed within the distal end and extending to the capsule cavity. The end cap extends from an end cap distal end to an end cap inner end and includes an air channel extending from the end cap distal end to the end cap inner end. Preferably, the air channel is non-parallel with the longitudinal axis. A capsule is contained within the capsule cavity. The capsule has a capsule length in a range from about 25% to about 99% of the cavity length, or about 50% to about 95% of the cavity length, or about 70% to about 90% of the cavity length, or from about 75% to about 85% of the cavity length, or about 80% of the cavity length.

The capsule cavity has a cavity inner diameter. The capsule has a capsule outer diameter. The capsule outer diameter may be in a range from about 80% to about 99% of the cavity inner diameter, or capsule outer diameter may be in a range from about 85% to about 95% of the cavity inner diameter, or capsule outer diameter may be about 90% of the cavity inner diameter.

The cavity length may be in a range from about 18 mm to about 22 mm and the capsule length may be in a range from about 14 to about 18 mm, or the cavity length may be in a range from about 19 mm to about 21 mm and the capsule length may be in a range from about 15 to about 17 mm, or the cavity length may be about 20 mm and the capsule length may be about 16 mm. The capsule outer diameter may be in a range from about 5.4 mm to about 6.4 mm and the cavity inner diameter may be in a range from about 6 mm to about 7 mm, or the capsule outer diameter may be in a range from about 5.7 mm to about 6.1 mm and the cavity inner may be may be in a range from about 6.4 mm to about 6.8 mm, or the capsule outer diameter is about 5.85 mm and the cavity inner diameter may be about 6.6 mm.

Advantageously, having the capsule and capsule cavity sized to the described dimensions may promote rotation of the capsule in the capsule cavity as air flows through the capsule cavity. Advantageously, the rotation is a stable rotation and the axis of rotation may be substantially coextensive with the longitudinal axis of the inhaler body. Advantageously, stable rotation of the capsule may provide a uniform entrainment of a portion or a fraction of nicotine particles from the capsule over two or more, or five or more, or ten or more inhalations or "puffs" by a consumer.

The airflow channel through the end cap may aid in rotation inducement of the contained capsule in the capsule cavity. Capsule rotation may assist in releasing nicotine particles (once the capsule is pierced) into the airflow through the inhaler article. Preferably there is more than one airflow channel through the end cap. The one or more airflow channels through the end cap may initiates "swirling" air flow though the capsule cavity and the physical dimensions of both the capsule cavity and the capsule may enhance the rotation of the capsule. An air channel extending along the end cap and being non-parallel with the longitudinal axis may advantageously initiate the "swirling" air flow through the capsule cavity.

Advantageously, providing the air channel along the length of the end cap provides an inhaler article that has a form similar to a conventional cigarette and an airflow configuration that is similar to a conventional cigarette. Advantageously, this inhaler article is simple to manufacture and convenient to use.

The end cap may include a piercing channel extending along the end cap longitudinal length. A resealable element may be disposed at either end of the piercing channel. The piercing channel may be co-axial with the longitudinal axis.

Advantageously, providing a piercing channel along the end cap allows reliable piercing of a capsule contained within the capsule cavity. Advantageously, the resealable element maintains the integrity of the desired air flow pattern within the capsule cavity.

A porous support element may separate the capsule cavity from the mouthpiece end. The porous support element may be a filter element. Airflow from the capsule cavity may flow through the porous support element to the mouthpiece end.

Advantageously, the porous support element allows entrained dry powder particles to freely pass through the porous support element while maintaining the physical dimensions of the capsule cavity. Advantageously, the porous support element may be a filter element that may be similar to a conventional plug of filter material utilized in conventional cigarettes. Advantageously, the porous support element may improve the desired air flow pattern through the capsule cavity.

The inhaler article described herein may provide a dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler may have a form similar to a conventional cigarette and may mimic the ritual of conventional smoking. This inhaler may be simple to manufacture and convenient to use by a consumer.

Air flow management through the capsule cavity may cause the capsule to rotate during inhalation and consumption. The capsule contains nicotine particles comprising nicotine (also referred to as "nicotine powder" or "nicotine particles") and optionally particles comprising flavour (also referred to as "flavour particles). Rotation of the pierced capsule may suspend and aerosolize the nicotine particles released from the pierced capsule into the inhalation air moving through the inhaler article. The flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler article at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg 151-197, and in the GRAS flavoring substances 27 S. M. Cohen et al., Food Technology Aug. 2015 pg. 40-59, and intervening GRAS Flavoring Substances publications 4 to 26. For the purpose of this disclosure, nicotine is not considered as a flavourant or flavour.

The inhaler article described herein may be combined with a piercing element or piercing device to deliver the nicotine particles to a consumer. The piercing element or piercing device may be separated from or not form a portion of the inhaler article. A plurality of these inhaler articles may be combined with a piercing element or piercing device to form a kit.

An inhaler article includes a body extending along a longitudinal axis from a mouthpiece end to a distal end and a capsule cavity defined within the body. The capsule cavity has a cavity length extending along the longitudinal axis. A mouthpiece air channel extends from the capsule cavity to the mouthpiece end. An end cap is disposed within the distal end and extends to the capsule cavity. The end cap extends from an end cap distal end to an end cap inner end. An air channel extends from the end cap distal end to the end cap inner end. A capsule having a capsule length is disposed within the capsule cavity. The capsule length is in a range from about 25% to about 99% of the cavity length, or about 50% to about 95% of the cavity length, or about 70% to about 90% of the cavity length, or from about 75% to about 85% of the cavity length, or about 80% of the cavity length. Preferably, the capsule length is in a range from about 75% to about 90% of the cavity length, in some preferred embodiments, the capsule length is in a range from about 80% to about 90% of the capsule length and in one preferred embodiment, the capsule length is about 88% of the cavity length.

The inhaler body may resemble a smoking article or cigarette in size and shape. The inhaler body may have an elongated cylindrical body extending along the longitudinal axis of the inhaler article. The inhaler body may have a substantially uniform outer diameter along the length of the elongated cylindrical body. The inhaler body may have a circular cross-section that may be uniform along the length of the elongated cylindrical body. The inhaler body may have an outer diameter in a range from about 6 mm to about 10 mm, or from about 7 mm to about 10 mm, or about 7 mm to about 9 mm, or about 8 mm. The inhaler body may have a length (along the longitudinal axis) in a range from about 40 mm to about 90 mm, or from about 50 mm to about 80 mm, or about 60 mm to about 70 mm, or 65 mm.

The air channel may be configured to induce a swirling air flow pattern within the capsule cavity of the inhaler body. The air channel may draw inlet air into the capsule cavity of the inhaler body from the end cap distal end. The air channel may induce rotational air flow or swirling air flow as the air flows through the air channels and through the capsule cavity. Air flow through the inhaler device preferably enters the inhaler device at the distal end face or end cap distal end of the inhaler device and moves along the longitudinal axis of the inhaler device to the mouthpiece end. Preferably, the air channel is non-parallel with the longitudinal axis. An inlet of the air flow channel may be defined within the end cap distal end face. The end cap distal end face may be orthogonal to the longitudinal axis of the inhaler device. Air flow may not pass thorough the elongated body of the inhaler body. There may be no air inlets through the elongated body of the inhaler body.

The air channel may be a channel element defined along an outer surface of the end cap and extending along a length of the end cap. The end cap may define three sides of the air channel. The end cap may define a bottom surface and opposing depth sides that define a depth of the air channel. The end cap may be inserted into the distal end of the inhaler body and form a portion of the distal end of the inhaler body. The distal end of the inhaler body may surround at least about 75%, or at least about 85% or at least about 90% or 100% of the length of the end cap. The distal end of the inhaler body may contain and hold the end cap in place within the distal end of the inhaler body.

The end cap may be inserted into the distal end of the inhaler body and may be fixed to the inhaler body by friction fit or an adhesive, for example. A distal end portion of the inhaler body may cooperate with the end cap air channel to enclose the air channel or form the remaining top surface of the air channel. The top surface may oppose the bottom surface defined by the end cap. The top surface and bottom surface may be parallel to each other. The opposing depth sides may be parallel to each other. The opposing top surface and bottom surface may be orthogonal to the opposing depth sides.

The air channel may extend a distance along an arc that is co-axial with the longitudinal axis. The air channel may be curved with respect the longitudinal axis of the inhaler device. The air channel may rotate around the circumference of the end cap as a function of a location along the end cap length. The air channel may rotate around about 25% to about 50% of the circumference. The air channel may rotate around the circumference of the end cap an arc length (distance when viewing the end cap from the distal end face) having a central angle (that may be coincident with the longitudinal axis of the inhaler body) in a range from about 45 degrees to about 180 degrees, or from about 45 degrees to about 135 degrees.

The air channel may enter the capsule cavity at an angle relative to the longitudinal axis. The air channel may enter the capsule cavity at an angle in a range from about 5 degrees to about 89 degrees, or about 45 degrees to about 89 degrees, or about 60 degrees to about 89 degrees, or about 70 degrees to about 88 degrees. The air channel may have a first portion parallel with the longitudinal axis and a second portion exiting into the capsule cavity at an angle relative to the longitudinal axis as described above.

The air channel may include at least two or two or more air channels formed into the end cap. The air channel may include at least three, or three or more air channels formed into the end cap. The air channels may be located symmetrically about the end cap. The air channels may oppose each other about the end cap along the end cap length. Preferably the one or more air channels are helical. The helical air channels may be symmetrically disposed along the end cap length and preferably oppose each other along the end cap length. The air channels may each extend a distance along an arc that are each co-axial with the longitudinal axis. The inhaler body may form the top surface for each air channel.

The end cap and air channel defined thereon may be precisely designed and manufactured to impart the desired air flow pattern through the capsule cavity of the inhaler device. This inhaler body and end cap may form a separate piece assembly that may provide for a simple and reliable manufacture and performance of the inhaler device.

The end cap may have an end cap length in a range from about 3 mm to about 12 mm, or from about 4 mm to about 10 mm, or from about 5 mm to about 9 mm, or about 7 mm. The end cap may have an outer diameter sufficient to form a close or friction fit with the inner diameter of the inhaler body. The end cap may have an outer diameter in a range from about 5 mm to about 10 mm, or from about 6 mm to about 9 mm, or about 6.5 mm to about 8.5 mm, or about 7.5 mm.

The end cap may include a collar element having a larger diameter than the remaining body of the end cap. The collar element may function as a physical stop to ensure proper placement of the end cap within the distal end portion of the elongated inhaler body. The collar may abut the elongated inhaler body. The collar may have a diameter that is about 0.5 mm to about 1 mm greater than the diameter than the remaining body of the end cap. The collar element may have a diameter that is substantially similar or the same as the outer diameter of the elongated inhaler body.

The end cap may include a linear piercing channel extending through the length of the end cap. The linear piercing channel may extend along a central axis of the end cap. The linear piercing channel may be co-axial with the longitudinal axis of the inhaler body. The linear piercing channel may be sized to allow a piercing element to pass through the linear piercing channel. The a linear piercing channel may have a diameter in a range from about 0.5 mm to about 2 mm.

The end cap may include a resealable element disposed on or within the linear piercing channel. The linear piercing channel includes a first end forming a portion of the end cap distal end and an opposing second end forming a portion of the end cap inner end. The resealable element may be disposed on or within end cap inner end. Alternatively or in addition, the resealable element may be disposed on or within the end cap distal end.

The resealable element may seal the linear piercing channel. The resealable element may form a hermetic or airtight seal or barrier along the linear piercing channel. The linear piercing channel may be formed of a pierce-able material. A piercing element may pass through the resealable element and puncture the capsule within the capsule cavity. The resealable element may reseal once the piercing element is retracted or removed from the resealable element. Resealable elements or membranes may include a septum or septum-like element. Resealable elements or membranes may be formed of elastic material such as rubber, silicone, metal foil co-laminated with a polymer, or latex and the like.

The capsule cavity may define a cylindrical space configured to contain a capsule (that may have an obround shape). The capsule cavity may have a substantially uniform or uniform diameter along the length of the capsule cavity. The capsule cavity may have a substantially cylindrical or cylindrical cross-section along the length of the capsule cavity. The configuration of the capsule cavity relative to the capsule may allow the capsule to rotate with stability within the capsule cavity. The longitudinal axis of the capsule may rotates with stability about the longitudinal axis of the inhaler body during inhalation. The length of the capsule cavity may form an airtight barrier Stable rotation refers to the longitudinal axis of the inhaler body being substantially parallel with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" by a consumer.

The capsule cavity may have a fixed cavity length. The capsule cavity may have a cavity length of about at least about 110% to less than about 300% of a length of the capsule contained therein, or in range from about 110% to about 200% of the capsule length, or from about 120% to about 130% of the capsule length, or about 125% of the capsule length. The capsule may have a length in a range from about 25% to about 99% of the cavity length, or about 50% to about 95% of the cavity length, about 70% to about 90% of the cavity length, or from about 75% to about 85% of the cavity length, or about 80% of the cavity length. The cavity length may be in a range from about 18 mm to about 22 mm and the capsule length may be in a range from about 14 to about 18 mm, or the cavity length may be in a range from about 19 mm to about 21 mm and the capsule length may be in a range from about 15 to about 17 mm, or the cavity length may be about 20 mm and the capsule length may be about 16 mm.

The capsule cavity has a cavity inner diameter, orthogonal to the longitudinal axis, and the capsule has a capsule outer diameter. The capsule outer diameter may be in a range from about 80% to about 99% of the cavity inner diameter, or capsule outer diameter may be in a range from about 85% to about 95% of the cavity inner diameter, or capsule outer diameter may be about 90% of the cavity inner diameter. The capsule outer diameter may be in a range from about 5.4 mm to about 6.4 mm and the cavity inner diameter may be in a range from about 6 mm to about 7 mm, or the capsule outer diameter may be in a range from about 5.7 mm to about 6.1 mm and the cavity inner diameter may be in a range from about 6.4 mm to about 6.8 mm, or the capsule outer diameter may be about 5.85 mm and the cavity inner diameter may be about 6.6 mm.

The capsule cavity may be bounded on an upstream side by the end cap and bounded on a downstream side by a porous support element. The end cap and porous support element cooperate to contain the capsule longitudinally within the capsule cavity. The porous support element may fill the inner diameter of the elongated inhaler body. The porous support element may allow air flow to exhibit a uniform airflow along the cross-section of the elongated inhaler body through the porous support element. The porous support element may function as a diffuser to reduce turbulence effects or edge effects and ensure or maintain the desired air flow pattern through the capsule cavity.

The porous support element may have a length that extends along the longitudinal axis a distance from about 20 mm to about 40 mm, or from about 22 mm to about 35 mm, or from about 25 mm to about 30 mm, or about 27 mm. The porous support element may have an outer diameter sufficient to form a friction fit with the inner diameter of the inhaler body. The porous support element may have an outer diameter in a range from about 5 mm to about 10 mm, or from about 6 mm to about 9 mm, or about 6.5 mm to about 8.5 mm, or about 7.5 mm.

The porous support element may define a filter element. The filter element may be formed of a network of fibres. The network of fibres may be a nonwoven fibre element. The porous support element may be a plug of filtration material. Fibres forming the porous support element may be derived from polylactic acid. Fibres forming the porous support element may be cellulose acetate. The filter element may be a plug of cellulose acetate or a plug of polylactic acid. The porous element may comprise a plastic mesh. The plastic mesh may have holes of from about 1 mm$^2$ to about 4 mm$^2$ or of about 2 mm$^2$.

The capsule may be sealed within the inhaler article prior to consumption. The inhaler article may be contained within a sealed or airtight container or bag. The inhaler article may include one or more peelable seal layers to cover the one or more air inlet channels or the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler. The capsule may formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 1 to size 4 capsule, or a size 3 capsule.

A separate piercing element, such as a metal or rigid needle, may form a single aperture through the capsule received in the capsule cavity. The piercing element may pass through the resealable element sealing the piercing channel on the end cap.

The capsule contains nicotine particles comprising nicotine (also referred to as "nicotine powder" or "nicotine particles") and optionally particles comprising flavour (also referred to as "flavour particles). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder.

The dry powder or powder system may have at least about 40%, or at least about 60%, or at least about 80%, by weight of the powder system comprised in nicotine particles having a particle size of about 10 micrometres or less, or 5 micrometers or less, or in a range from about 1 micrometer to about 3 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include flavour particles. The flavour particles may have any useful size distribution for inhalation delivery selectively into the mouth or buccal cavity of a user.

The powder system may have at least about 40%, or at least about 60%, or at least about 80%, by weight of the flavour of the powder system comprised in particles having a particle size of about 20 micrometres or greater. The powder system may have at least about 40% or at least about 60%, or at least about 80%, by weight of the flavour of the powder system comprised in particles having a particle size of about 50 micrometres or greater. The powder system may have at least about 40% or at least about 60%, or at least about 80%, by weight of the flavour of the powder system comprised in particles having a particle size in a range from about 50 micrometer to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. The flavour or flavourant has flavour properties that may enhance the experience of the nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called “puff-inhale-exhale”.

All scientific and technical terms used herein have meanings commonly used in the art unless otherwise specified. The definitions provided herein are to facilitate understanding of certain terms used frequently herein.

The terms “upstream” and “downstream” refer to relative positions of elements of the inhaler described in relation to the direction of inhalation air flow as it is drawn through the body of the inhaler from a distal end portion to the mouthpiece portion.

As used herein, the singular forms “a”, “an”, and “the” encompass embodiments having plural referents, unless the content clearly dictates otherwise.

As used herein, “or” is generally employed in its sense including “and/or” unless the content clearly dictates otherwise. The term “and/or” means one or all of the listed elements or a combination of any two or more of the listed elements.

As used herein, “have”, “having”, “include”, “including”, “comprise”, “comprising” or the like are used in their open ended sense, and generally mean “including, but not limited to”. It will be understood that “consisting essentially of”, “consisting of”, and the like are subsumed in “comprising,” and the like.

The words “preferred” and “preferably” refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIG. 1 is a perspective view of an illustrative inhaler article.

FIG. 2 is a cross-sectional schematic diagram of the illustrative inhaler article of FIG. 1 along the longitudinal axis.

FIG. 3A and FIG. 3B are perspective views of an illustrative end cap.

FIG. 4A and FIG. 4B are perspective views of another illustrative end cap.

FIG. 5 is a cross-sectional schematic diagram of another illustrative end cap.

FIG. 6 is cross-sectional schematic diagram of another illustrative end cap.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

FIG. 1 and FIG. 2 illustrate an exemplary inhaler article 100. FIG. 2 is a cross-sectional schematic diagram of the illustrative inhaler article of FIG. 1 along the longitudinal axis. The inhaler article 100 includes a body 110 extending along a longitudinal axis $L_A$ from a mouthpiece end 112 to a distal end 114 and a capsule cavity 116 defined within the body 110. A mouthpiece air channel 111 extends from the capsule cavity 116 to the mouthpiece end 112. An end cap 120 is disposed within the distal end 112 and extends to the capsule cavity 116. The end cap 120 extends from an end cap distal end 124 to an end cap inner end 122 an end cap length. The end cap 120 includes an air channel 113 extending from the end cap distal end 124 to the end cap inner end 122. The air channel 113 is non-parallel with the longitudinal axis $L_A$.

The end cap inner end 122 and a porous support element 140 bound the capsule cavity 116. A capsule 130 is disposed within the cavity 116. The capsule 130 contains particles comprising nicotine. The end cap 120 and the porous support element 140 cooperate to contain the capsule 130 longitudinally within the capsule cavity 116. The mouthpiece end 112 is illustrated having a recessed end where the body 110 bounds an open space at the mouthpiece end 112. Alternatively the porous support element 140 can extend to the mouthpiece end 112 to fill the entire mouthpiece end 112.

The capsule cavity 116 has a cavity length $L_1$ extending along the longitudinal axis $L_A$. The capsule 130 has a capsule length $L_2$. The capsule cavity has a cavity inner diameter $D_1$. The capsule 130 has a capsule outer diameter $D_2$. The capsule 130 axis of rotation may be coextensive with the longitudinal axis $L_A$.

FIG. 3A to FIG. 4B illustrate opposing curved, or helical air channels 113 rotating about the circumference as a function of a location along the length of the end cap 120. The end cap 120 may include a collar element 125 having a larger diameter than the remaining body 123 of the end cap 120.

FIG. 3A, FIG. 4A, FIG. 5 and FIG. 6 illustrate a linear piercing channel 121 extending through the length of the end cap 120. The linear piercing channel 121 may extend along a central axis of the end cap 120.

FIG. 4B, FIG. 5 and FIG. 6 illustrate a resealable element 129 disposed on or within the linear piercing channel 121. FIG. 4B and FIG. 5 illustrate a resealable element 129 disposed on the end cap inner end 122 and sealing the linear piercing channel 121. FIG. 6 illustrates a resealable element 129 disposed on the end cap distal end 124 and sealing the linear piercing channel 121.

A separate piercing element (not shown) may be utilized by a consumer to pierce the resealable element 129 along the linear piercing channel 121 and puncture the capsule 130 contained within the capsule cavity 116. The piercing element may be withdrawn from the inhaler article 100 to reseal the resealable element 129. A consumer may then utilize the inhaler device.

The invention claimed is:

1. An inhaler article comprising:
    a body extending along a longitudinal axis from a mouthpiece end to a distal end;
    a capsule cavity defined within the body, the capsule cavity having a cavity length extending along the longitudinal axis;
    a mouthpiece air channel extends from the capsule cavity to the mouthpiece end;
    an end cap disposed within the distal end and extending to the capsule cavity, the end cap extending from an end cap distal end face to an end cap inner end and comprising a helical air channel extending from the end cap distal end face to the end cap inner end and a linear piercing channel and a resealable element disposed on or within the linear piercing channel; and
    a capsule disposed within the capsule cavity, the capsule having a capsule length, the capsule length is in a range from about 25% to about 99% of the cavity length.

2. The inhaler article according to claim 1, wherein the capsule contains particles comprising nicotine.

3. The inhaler article according to claim 1, wherein the cavity length is in a range from about 18 mm to about 22 mm and the capsule length is in a range from about 14 to about 18 mm.

4. The inhaler article according to claim 1, wherein the capsule cavity has a cavity inner diameter, orthogonal to the longitudinal axis, and the capsule has a capsule outer diameter, and the capsule outer diameter is in a range from about 80% to about 99% of the cavity inner diameter.

5. The inhaler article according to claim 4, wherein the capsule outer diameter is in a range from about 85% to about 95% of the cavity inner diameter.

6. The inhaler article according to claim 5, wherein the capsule length is in a range from about 75% to about 85% of the cavity length.

7. The inhaler article according to claim 1, wherein the capsule cavity has an cavity inner diameter, orthogonal to the longitudinal axis, and the capsule has an capsule outer diameter that is less than the cavity inner diameter, and the capsule outer diameter is in a range from about 5.4 mm to about 6.4 mm and the cavity inner diameter is in a range from about 6 mm to about 7 mm, or the capsule outer diameter is in a range from about 5.7 mm to about 6.1 mm and the cavity inner diameter is in a range from about 6.4 mm to about 6.8 mm, or the capsule outer diameter is about 5.85 mm and the cavity inner diameter is about 6.6 mm.

8. The inhaler article according to claim 1, wherein the capsule cavity has a uniform or constant diameter along the cavity length.

9. The inhaler article according to claim 1, wherein the capsule cavity is a fixed length.

10. The inhaler article according to claim 1, wherein the air channel comprises at least two air channels that are symmetrical.

11. The inhaler article according to claim 10, wherein the at least two air channels oppose each other along the end cap length.

12. The inhaler article according to claim 1, comprising a second helical air channel extending from the end cap distal end face to the end cap inner end.

13. The inhaler article according to claim 1, wherein the body has an outer diameter that is substantially constant from the distal end to the mouthpiece end.

14. The inhaler article according to claim 1, further comprising a filter element disposed within the body and separating the capsule cavity from the mouthpiece end, the filter element in air flow communication with the capsule cavity and the mouthpiece air channel.

15. The inhaler article according to claim 14, wherein the filter element comprises fibres derived from polylactic acid.

16. The inhaler article according to claim 14, wherein the filter element defines a downstream end of the capsule cavity.

17. The inhaler article according to claim 1, wherein the capsule length is in a range from about 50% to about 95% of the cavity length.

18. The inhaler article according to claim 1, wherein the capsule length is in a range from about 75% to about 85% of the cavity length.

19. A method comprising:
    flowing air through the inhaler article according to claim 1, such that the flowing air spins the capsule about the longitudinal axis.

20. The method according to claim 19, wherein the flowing air has a flow rate in a range from about 2 L/min to about 1 L/min.

* * * * *